US00PP33314P3

(12) United States Plant Patent
Meyer

(10) Patent No.: US PP33,314 P3
(45) Date of Patent: Aug. 3, 2021

(54) ***HEMEROCALLIS* PLANT NAMED 'SOUND OF MY HEART'**

(50) Latin Name: ***Hemerocallis* (L.) hybrid**
Varietal Denomination: Sound of My Heart

(71) Applicant: Chris Meyer, Zeeland, MI (US)

(72) Inventor: Chris Meyer, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/602,733

(22) Filed: Nov. 26, 2019

(65) Prior Publication Data

US 2021/0161047 P1 May 27, 2021

(51) Int. Cl.

| | |
|---|---|
| ***A01H 5/02*** | (2018.01) |
| ***A01H 6/00*** | (2018.01) |
| ***A01H 6/56*** | (2018.01) |

(52) U.S. Cl.
USPC ..... Plt./312
CPC ..... *A01H 6/00* (2018.05); *A01H 6/56* (2018.05)

(58) Field of Classification Search
USPC ..... Plt./312
CPC ..... A01H 5/02
See application file for complete search history.

*Primary Examiner* — Kent L Bell

(57) ABSTRACT

A new and distinct *Hemerocallis* plant named 'Sound of My Heart' characterized by winter-hardy compact habit with clean medium-green foliage that goes dormant in the winter. The flowers are rounded, fragrant, single, pastel-pink, with a wide wine-purple band and matching picotee edge and yellow to light green throat. Outer and inner tepal sets are slightly reflexed with the inner tepal set having consistent, considerable, wine purple crisped margins. The new plant flowers on stems up to 70 cm tall with four-way branching beginning about mid-July and repeating into October.

1 Drawing Sheet

Botanical classification: *Hemerocallis* (L.) hybrid.
Variety denomination: 'Sound of My Heart'.

STATEMENT REGARDING PRIOR DISCLOSURES UNDER 37 CPR 1.77(B)(6)

The first disclosure, in the form of a sale, was made by Walters Gardens, Inc. on May 6, 2019 to Overdevest Nurseries, L.P., Gardens Alive and Prides Corner. On Dec. 1, 2018 a photograph and brief description of the new plant were also placed on a website of Walters Gardens, Inc. and on May 29, 2019 the new plant was advertised in the "Walters Gardens 19-20 Catalog". Walters Gardens, Inc. obtained the new plant and all information relating thereto, from the inventor. No plants of *Hemerocallis* 'Sound of My Heart' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to a new and distinct daylily plant, *Hemerocallis* 'Sound of My Heart' hereinafter also referred to as the new plant or just the cultivar name, 'Sound of My Heart'. *Hemerocallis* 'Sound of My Heart' was hybridized by the inventor, Chris Meyer, in the spring of 2006 in a greenhouse at a wholesale perennial nursery in Zeeland, Mich., USA. The new plant originated from a breeding program conducted by the inventor with the specific intention to improve the garden worthiness, expand color regimens and increase flowering period which were some of the criteria of further trials in the trial beds at the same nursery in Zeeland, Mich. The female or seed parent was 'Spiny Sea Urchin' (not patented) and the male or pollen parent was 'Rock Solid' (not patented). The new plant was selected as a single seedling from this cross, and after confidential evaluations in a trial bed beginning in 2008 in Zeeland, Mich. was assigned the breeder code 06-290-7. The new plant has been asexually propagated by division at the same wholesale nursery in Zeeland, Mich. since 2009 with all resultant asexually propagated plants having retained all the same unique traits as the original plant. *Hemerocallis* 'Sound of My Heart' is stable and reproduces true to type in successive generations of asexual reproduction.

There are nearly 90,000 registered daylilies with The American *Hemerocallis* Society, which is the International Cultivar Registration Authority for the genus *Hemerocallis*. In comparison to the new plant, the female parent has a pastel lavender flower color with a yellow watermark, a yellow-gold braided edge and a green throat. In comparison to the new plant, the male parent has a creamy flower with a very large plum-violet eye with a gold spiny edge on the inner tepal set and a green throat.

The most similar daylily cultivars known to the inventor are 'Angelic Enchantment' (not patented), 'Pink Puzzler' (not patented), 'Inwood' (not patented) and 'Daring Deception' (not patented).

'Angelic Enchantment' has taller flower stems and larger flowers with tepals that are deeper pink with a purple eye and picotee margin that are thinner and lighter colored. 'Pink Puzzler' has taller flower stems with larger flowers that more recurved tepals with faintly colored midribs, thinner eye zone, gold throat and a gold picotee margin. 'Inwood' has larger flowers with a peachy-cream base, a thinner purple eye-zone and green throat on slightly shorter scapes. 'Daring Deception' has flowers with a dusky cream-pink base, narrower and lighter purple eye zone on slightly short stems.

*Hemerocallis* 'Sound of My Heart' differs from all other daylilies known to the applicant, by the combination of the following traits:

1. Winter-hardy, compact habit with clean medium-green foliage that goes dormant in the winter;
2. Fragrant, single, limbate, rounded flowers about 15 cm across of pastel-pink with a very wide wine-purple band and matching ruffled picotee edge and yellow to light green throat;
3. Inner tepals with consistent, considerable, wine-purple crisped margins.
4. Inner and outer tepals slightly reflexed;
5. Plants produce four-way branched scapes of about 70 cm tall with up to 28 flowers per scape;
6. Flowering begins about mid-July with excellent coverage with repeat flowering late in the season;

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
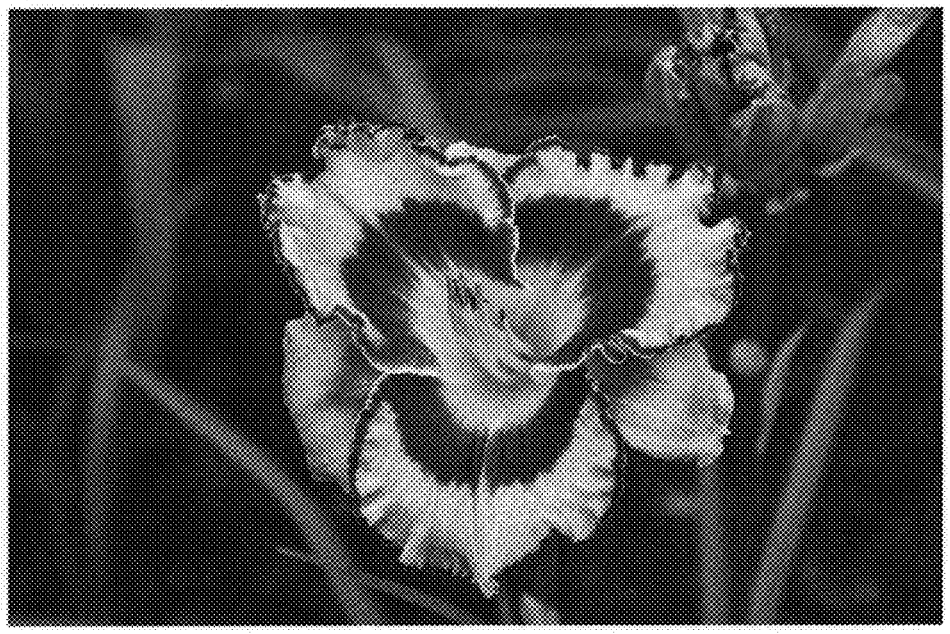
FIG. 1 shows a close-up of the flower.
Figure 2:
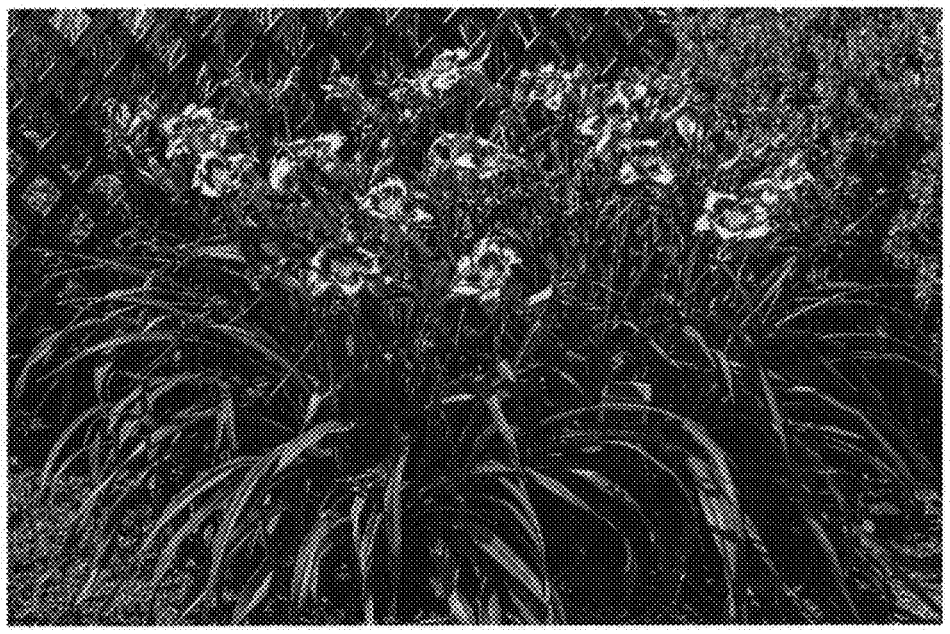
FIG. 2 shows a group of three-year-old plants in peak flower in a sunny landscape during mid-summer at a display garden in Zeeland, Mich.

The following descriptions and color references are based on the 2015 edition of The Royal Horticultural Society Colour Chart except where common dictionary terms are used. The new plant, *Hemerocallis* 'Sound of My Heart', has not been observed under all possible environments. The phenotype may vary slightly with different environmental conditions, such as temperature, light, fertility, moisture and maturity levels, but without any change in the genotype. The following observations and size descriptions are of a three-year-old plant in a sunny landscape at a display garden in Zeeland, Mich. with and supplemental water and fertilizer.

Botanical classification: *Hemerocallis* (L.) hybrid;

Parentage: Female (seed) parent is 'Spiny Sea Urchin'; male (pollen) is 'Rock Solid' (not patented);

Propagation: Division of the rhizome;

Growth rate: Moderate to rapid;

Crop time: About 8 to 10 weeks to flower starting in spring in a 3.8 liter container from vernalized one-year-old plant;

Rooting habit: Fleshy, about 2.5 mm diameter; lightly branching;

Root color: Nearest RHS 159C depending on soil type;

Plant shape and habit: Winter-hardy herbaceous perennial with four basal shoots emerging from rhizomes producing a radially symmetrical mound of arching leaves;

Plant size: Foliage height about 42.0 cm tall from soil line to the top of the leaves and about 86.0 cm wide at the widest point;

Leaves: Entire, glabrous, slightly glaucous abaxial and adaxial, linear, sessile; folded; apex narrowly acute, base sheathing; to about 59.0 cm long and 32.0 mm across, average about 55.0 cm long and about 29.0 mm across; about 20 leaves per division;

Cauline leaves: 1 to 2 per scape; reduced, average about 4.0 cm long and 10.0 mm across;

Leaf color: Young abaxial and adaxial nearest RHS 146C; mature adaxial between RHS 146B and RHS 138A, mature abaxial nearest RHS 146B;

Veins: Parallel; color abaxial nearest RHS 137A and adaxial between RHS 137A and RHS 138A;

Flower description:

Flowers: Funnelform; single, with two sets of three tepals; zygomorphic, incomplete; up to 28 per scape, mostly distally arranged on typically 4 branches; upward and outwardly facing; about 13.3 cm across and 10.5 cm tall to exserted stigma, corolla about 7.5 cm deep; corolla tube diameter at fusion about 1.3 cm, length from base to fusion point about 1.3 cm long; individually lasting for about one day; peduncle remains effective from mid-July into early-August for approximately three weeks in Zeeland, Mich. with repeating into October;

Inflorescence: Upwardly, erect; to about 70 cm tall and flowering to about 25 cm across;

Flower fragrance: Lightly sweet;

Buds one day prior to opening: Oblate ellipsoid with bluntly acute apex and tepals beginning to separate, and basal one-fifth narrowed terete; about 88.0 mm long and about 22.0 mm in diameter at widest point with basal one-fifth narrowing to about 11.0 mm diameter;

Buds two days prior to opening: About 72.0 mm long and 20.0 mm diameter;

Bud color one day from opening: Exposed apex variable mixture of RHS 157B, RHS NN155C, and N186C; abaxial apical 3.0 mm nearest RHS 137B, central portion along tepal margins nearest RHS 185C, central portion distally nearest RHS 144A, middle nearest blend of RHS 185C and RHS 146D, basal 15 mm nearest RHS 146C;

Tepals: 2 sets of 3;

Inner tepals: Glabrous; rounded apex; consistently and considerably crisped margins to about 1.0 cm deep; base truncate, fused in proximal 3.0 cm; width at fusion about 5.0 mm; midrib fluted about 2.0 mm on adaxial and costate on abaxial surface; recurved 90 degrees in distal one-fifth; about 7.0 cm across at widest point and about 11.8 cm long;

Outer tepals: Glabrous; acute apex; irregularly and slightly wavy to crisped outer margin to about 7.0 mm, central portion of outer tepal irregularly undulate; tepals reflexed about 90 degrees in distal one-fifth; fused in proximal 3.0 cm; about 10.3 cm long and 4.8 cm across;

Inner tepal color adaxial starting distally: Outer about 1.0 mm wide nearest RUS 162D with next inner portion of margin about 3 mm wide nearest RHS 187A; distally center inside margin between RHS 291D and RHS 24D; eye zone about 22.0 mm wide nearest a blend between RHS N77B and RHS N77A along with nearest a blend between RHS N79B and RHS N79A; throat distally nearest RHS 4A transitioning to nearest RHS 154A proximally;

Inner tepal color abaxial: Outer margin about 1.0 mm wide nearest blend of RHS 18A and RHS 18B next proximal portion of martin about 2.0 mm wide nearest RHS 187A; distal blade between RHS 179D and RHS 186D; proximal basal edges nearest RHS 11D with basal center nearest RHS 2C;

Outer tepal color adaxial: Between RHS 29A and RHS 24A distally irregularly blotched with nearest RHS 181D, center eye zone blushed with RHS N79B; throat nearest RHS 4A distally and RHS 154A proximally;

Outer tepal color abaxial: 3.0 mm apex nearest RHS 138A; distal edges between RHS 186C and RHS 186D, center nearest RHS 24A and 2C, proximally between RHS 145A and RHS 146D;

Pedicel: Cylindrical; slightly glaucous; approximately 10.0 mm long, 6.0 mm wide at base;

Pedicel color: Nearest blend between RHS 138A and RHS 146B;

Peduncle: Usually three per plant during peak initial flowering and two per plant with repeat flowering, erect to about 70.0 cm tall and 8.0 mm diameter at base, average 65.0 cm tall; slightly glaucous; cylindrical; extending above foliage;

Peduncle color: Nearest blend between RHS 138A and RHS 146B;

Gynoecium: Single; tri-carpelled; glabrous; about 10.7 cm long;

*Style*.—Single, about 9.5 cm long, 2.0 mm diameter, curled upward at distal one-third; color distally nearest RHS 25D, middle nearest RHS 4C and proximally nearest RHS 2D.

*Stigma*.—1.0 mm to 2.0 mm in diameter; color nearest RHS 163D.

*Ovary*.—Ellipsoidal; smooth; acute apex, truncate base; about 9.0 mm long and 5.0 mm diameter at base; color nearest RHS 145A.

Androecium: Six; glabrous;

*Filaments*.—Six; cylindrical; adnate to inner tepal in basal 20.0 mm above ovary; arcuate upward in distal 10 mm; free in distal 48.0 mm long from fusion point on tepal; 68.0 mm long and basally applanate, 4.0 mm across and 2.0 mm thick; color distally nearest RHS between RHS 29C and RHS 159A, center nearest RHS 10C and proximally nearest RHS 2A.

*Anthers*.—Oblong; dorsifixed, longitudinal; about 10.0 mm long and 2.0 mm wide; color closest to RHS N187A.

*Pollen*.—Elliptical, less than 0.1 mm long; color nearest RHS 17A.

Fruit and seeds have not been observed;

Disease and pest resistance and tolerance: 'Sound of My Heart' has not shown resistance to diseases and pests beyond that common for daylilies, and given the northern testing regions the new plant has not been exposed to daylily rust, *Puccinia hemerocallidis*. The plant grows best and shows best coloration with plenty of moisture, adequate drainage and light shade during the hottest period of the day, but is able to tolerate some drought when mature and direct sun without leaf burn when provided sufficient water.

Hardiness at least from USDA zone 3 through 9, and other disease resistance and tolerance is typical of that of other daylilies. The new plant is useful for landscaping en masse, as a single specimen or small groups.

The invention claimed is:

1. A new and distinct ornamental daylily plant named *Hemerocallis* 'Sound of My Heart' as herein described and illustrated.

* * * * *